United States Patent
Kammerer (10) Patent No.: US 11,578,352 B2
(45) Date of Patent: Feb. 14, 2023

(54) TEST SPECIMEN, TEST CHAMBER, USE AND METHOD

(71) Applicant: Aesculap AG, Tuttlingen (DE)

(72) Inventor: Selina Kammerer, Dauchingen (DE)

(73) Assignee: AESCULAP AG, Tuttlingen (DE)

( * ) Notice: Subject to any disclaimer, the term of this patent is extended or adjusted under 35 U.S.C. 154(b) by 0 days.

(21) Appl. No.: 16/425,663

(22) Filed: May 29, 2019

(65) Prior Publication Data

US 2019/0376109 A1     Dec. 12, 2019

(30) Foreign Application Priority Data

Jun. 8, 2018 (DE) ..................... 10 2018 209 116.1

(51) Int. Cl.
| | | |
|---|---|---|
| *C12Q 1/06* | (2006.01) | |
| *C12Q 1/22* | (2006.01) | |
| *B01L 3/00* | (2006.01) | |
| *C12M 1/12* | (2006.01) | |

(52) U.S. Cl.
CPC ............ *C12Q 1/06* (2013.01); *B01L 3/50853* (2013.01); *C12M 25/06* (2013.01); *C12Q 1/22* (2013.01); *B01L 2300/042* (2013.01); *B01L 2300/0809* (2013.01); *B01L 2300/0851* (2013.01); *B01L 2300/0858* (2013.01)

(58) Field of Classification Search
None
See application file for complete search history.

(56) References Cited

U.S. PATENT DOCUMENTS

2005/0191750 A1    9/2005   Dunkelberg

FOREIGN PATENT DOCUMENTS

| | | | |
|---|---|---|---|
| CN | 101177661 | 5/2008 | |
| CN | 203999617 | 12/2014 | |
| DE | 102 13 361 | 1/2004 | |
| DE | 102 61 627 | 7/2004 | |
| DE | 10261627 A1 * | 7/2004 | ............... A61L 2/28 |
| WO | 2004101006 | 11/2004 | |

OTHER PUBLICATIONS

Dunkelberg, H. in EngMT. Device fortesting sterile conditions of packed medical units, designed as a chamber with various testing facilities. German patent application DE10261627A1. Date of Pub.: Jul. 22, 2004, pp. 1-8; specif, pp. 3, 5, 6.*
Chen, P. et al. Apr. 2017. Review: Bioaerosol collection. International Journal of Plasma Environmental Science & Technology 11(1) : 52-55. specif, pp. 52, 53.*
Abdullah, J.M. et al. 2009. "System 48" high-throughput cloning and protein expression analysis. Methods in Molecular Biology 498: 117-127; NIH Public Access numbering 1-9. specif, pp. 1, 4, 5.*
Raynaud, X. et al. 2014. Spatial ecology of bacteria at the microscale in soil. PLoS ONE 9(1): 1-9. specif, pp. 1, 2, 4, 6.*
Chinese Office Action dated Apr. 12, 2021, of corresponding Chinese Patent Application No. 201910492571.4.

* cited by examiner

*Primary Examiner* — Renee Claytor
*Assistant Examiner* — Sharon M. Papciak
(74) *Attorney, Agent, or Firm* — Lewis Kohn & Walker LLP; David M. Kohn (57) ABSTRACT

A test specimen for detecting or determining a spatial distribution of microbes, the test specimen having measuring surfaces and a plurality of microbe collecting elements on each of the measuring surfaces. The invention also relates to a test chamber with such a test specimen, to an associated use and to an associated method.

8 Claims, 5 Drawing Sheets

TEST SPECIMEN, TEST CHAMBER, USE AND METHOD

This application is a United States Non-provisional Application claiming priority under 35 U.S.C. § 119 from German Patent Application No. DE 10 2018 209 116.1 filed Jun. 8, 2018, the entire contents of which are herein incorporated by reference.

The invention relates to a test specimen for detecting and/or determining a spatial distribution of microbes or germs and to an associated test chamber, to an associated use and to an associated method.

Products in the medical sector, such as for example sterile product packagings, are often sterilized and packed at a central location and then transported to places of use. For example, transport may take place within a hospital, which involves a difference in elevation, and as a result a change in pressure. Furthermore, transport may take place by means of road vehicles, such as for example trucks.

It is important in this case that a microbial barrier effect is completely retained even during such transporting operations. Therefore, products such as sterile product packagings are typically subjected to tests that test the microbial barrier properties under changing conditions, such as for example different pressures.

Test chambers for this purpose are known in the prior art, for example from the document DE 102 61 627 A1. Although such test chambers allow products to be exposed to microbial contamination and different pressures, it has been found to be problematic that known methods of detection do not provide any information about microbe distribution in three-dimensional space, i.e. whether or not the product has been exposed to microorganisms from all sides, in particular uniformly.

As a result, it is possible for example that predominantly only the locations of a product that can be reached by sedimentation are exposed to microorganisms, which may have the effect that only partial testing of the product takes place and possible weak points are not tested sufficiently.

The invention therefore addresses the problem of developing measures that allow better monitoring of a microbe distribution within a test chamber.

This is achieved according to the invention by a test specimen, a test chamber, a use and a method according to the respective main claims. Advantageous refinements can be taken for example from the respective subclaims. The content of the claims is made the content of the description by express reference.

The invention relates to a test specimen for detecting and/or determining a spatial distribution of microbes, in particular in a test chamber, preferably in a test chamber during the microbial barrier testing of a product. The test specimen has a number of measuring surfaces. A plurality of microbe collecting elements are respectively arranged on each of the measuring surfaces.

The microbe collecting elements are respectively designed to collect microbes, in particular on microbe detecting elements, which—as still to be explained below—may be arranged behind each measuring surface.

The expression "microbes" or "germs" is intended within the context of the present invention to be understood as meaning microorganisms, in particular pathogenic microorganisms (so-called pathogens). In particular, the expression "microbes" or "germs" is intended within the context of the present invention to be understood as meaning bacteria and/or fungi and/or algae and/or viruses and/or subcellular structures, such as for example proteins and/or nucleic acids.

The expression "test chamber" is intended within the context of the present invention to be preferably understood as meaning a chamber within which products can be tested for microbial barrier properties.

The expression "product" is intended within the context of the present invention to be understood as meaning in particular a sterile product packaging and/or a packaged, in particular sterile-packaged, medical product. The medical product may be in particular a surgical instrument.

The expression "sterile product packaging" is intended within the context of the present invention to be understood as meaning a packaging for a medical product that is to be sterilized or is already in a sterile state.

By means of the test specimen according to the invention, a determination of the microbes present can be performed at multiple positions, in particular at each microbe collecting element. Since a measuring surface is a two-dimensional object that extends through a three-dimensional space, a distribution of microorganisms in space is thereby determined.

The test specimen may for example have a single measuring surface or a plurality of measuring surfaces, i.e. multiple measuring surfaces. This should be understood here as meaning a number of measuring surfaces. In the case of multiple measuring surfaces, each measuring surface preferably has the same number of microbe collecting elements.

According to a preferred configuration, the test specimen has the form of a cuboid. Preferably, one side of the cuboid in this case forms a bottom face of the test specimen and five sides of the cuboid form respective measuring surfaces. As a result, a three-dimensional measurement on all sides is made possible.

The cuboid may in particular be a cube. This has proven to be advantageous for typical applications.

Furthermore, the test specimen may have a seal, in particular in the form of a round silicone cord seal, between the bottom face and the respective faces having measuring surfaces. As a result, an undesired penetration of microbes into the interior of the test specimen can be prevented along these regions of the test specimen.

The test specimen may alternatively also have the form of a sphere or the form of a segment of a sphere. This also allows a three-dimensional distribution of microbes to be determined in an advantageous way.

According to an advantageous configuration, the test specimen may have a bottom face and a number of measuring surfaces arranged on it, at least partially sloping in relation to the bottom face. A sloping alignment achieves the effect that microbes can fall from above onto multiple microbe collecting elements arranged on the sloping measuring surface.

Also, in the case of this configuration, the test specimen may have a seal, in particular in the form of a round silicone cord seal, between the bottom face and respective faces having measuring surfaces.

According to one possible configuration, each microbe collecting element is formed as a through-hole through the respective measuring surface. Such a through-hole allows the respective microbes to penetrate into the interior of the test specimen and be detected in a suitable way.

According to an advantageous configuration, the test specimen has a respective holding device for a microbe detecting element behind each measuring surface. Such a microbe detecting element may be in particular a plate or a dish with a solid or liquid nutrient medium. The nutrient medium may for example be selected from the group consisting of agar, CASO agar, CASO bouillon, Columbia blood agar and mixtures thereof. As a result, a microbe monitoring can be achieved for example by the microbes passing through a respective microbe collecting element in the form of a through-hole and remaining attached to the respective microbe detecting element in the form of a plate coated with a nutrient medium. The formation of colonies for detecting the microbes is possible there.

Preferably, a respective microbe detecting element is in this case secured in each holding device, preferably directly adjacent to the through-holes. This allows an efficient collection of microbes and also a clear delimitation of the microbes passing through the different through-holes, which makes an evaluation of a three-dimensional or two-dimensional microbe distribution possible.

Preferably, the respective microbe detecting element is coated with agar or some other nutrient medium on a side facing the through-holes. As a result, captured microbes can be cultivated directly on the microbe detecting element, in particular after a corresponding testing operation. As a result, microbes can be detected in an advantageous way. It should however be mentioned that it is possible for the microbes just to be collected by means of the microbe detecting elements and that they can be detected in some other way, or by means of a later transfer to a nutrient medium, for example by carrying out the so-called surface spatula method.

According to one possible configuration, each microbe collecting element is formed as a respective vessel that is secured on the measuring surface. As a result, microbes can be collected in a respective vessel, which can be used afterwards for the evaluation.

Each vessel is preferably assigned a cover, by means of which the vessel can be closed, preferably can be closed in a germ-proof manner. As a result, the respective vessel can be closed in particular while the test specimen is being introduced into a test chamber and after carrying out a test, so that microbes are only collected while a test is actually being carried out. The closure of the respective vessel may be based on a threaded closure or a snap-fit closure.

Preferably, each vessel is produced from glass or a metal material, in particular from a glass or metal material that is suitable for carrying out sterilization, in particular steam sterilization.

It should be understood that the embodiments of microbe collecting elements described herein can also be combined with one another in any way desired. For example, some measuring surfaces may be provided with microbe collecting elements configured as through-holes, while other measuring surfaces may be provided with microbe collecting elements formed as vessels. Also, different configurations may be used within one measuring surface.

The invention also relates to a test chamber for testing a product for microbial barrier properties, at least one test specimen according to the invention being arranged in the test chamber. With regard to the test specimen, it is possible to fall back on all of the configurations and variants described herein. Similarly, multiple test specimens may be used.

By means of the test chamber according to the invention, the advantages of a test specimen described further above can be made usable for a test chamber for the microbial barrier testing of a product, in particular a sterile product packaging and/or a packaged medical product, preferably a sterile-packaged medical product.

The invention also relates to a use of a test specimen according to the invention for determining a spatial microbe distribution, in particular in a test chamber, preferably in a test chamber when testing a product for microbial barrier properties. As a result, it is possible in an advantageous way to determine a spatial microbe distribution that provides information on whether the product was exposed to a desired spatial microbe distribution, and consequently allows an assessment as to whether the product has been tested in a desired or sufficient way. With regard to the test specimen used, it is possible to fall back on all of the configurations and variants described herein.

The invention also relates to a method for determining a spatial microbe distribution, in particular in a test chamber, preferably in a test chamber when testing a product for microbial barrier properties, the method comprising the following steps:

introducing a test specimen according to the invention into a test chamber, it being possible with regard to the test specimen to fall back on all of the configurations and variants described herein, introducing a number of products into the test chamber, introducing microbes into the test chamber, producing proliferating conditions for microbes collected by the microbe collecting elements for the cultivation of the microbes, counting cell colonies that have grown and determining the spatial microbe distribution on the basis of numbers of cell colonies that have grown.

By means of the method according to the invention, a spatial microbe distribution can be determined in an advantageous way in a test chamber when testing for microbial barrier properties. In this case, it is possible to fall back on the known and tried methods of cultivating and counting cell colonies for determining respective numbers of microbes.

The test specimen may in this case be formed for example with through-holes as microbe collecting elements, and the through-holes may be closed before the introduction of the test specimen into the test chamber and at least partially opened again after introduction. This prevents microbes from passing through the through-holes already before the beginning of the actual testing, which may distort the result of the measurement. After carrying out a test, the through-holes are preferably closed again, in order likewise to avoid the depositing of undesired microbes. The closing of the through-holes may be performed for example with the aid of plugs (stoppers), in particular silicone plugs (silicone stoppers).

Preferably, the test specimen is sterilized before it is introduced into the test chamber. In particular, the test specimen may be subjected to a steam sterilization before it is introduced into the test chamber.

The test specimen may also be formed for example with vessels as microbe collecting elements, the vessels preferably being closed before the introduction of the test specimen into the test chamber and at least partially opened again after introduction, microbes collected in the vessels being diluted with a diluting liquid after the microbial barrier testing, and the cultivation being carried out with the diluted microbes. As a result, the number of microbes collected in the respective vessels during the testing operation can be determined in an advantageous way, which provides information on a spatial microbe distribution.

Generally, the proliferating conditions for the microbes collected by the microbe collecting elements (for the cultivation of the microbes) are produced outside the test chamber. In other words, the cultivation of the microbes collected by the microbe collecting elements is generally carried out outside the test chamber.

If a test specimen with through-holes as microbe collecting elements is used, it is possible for example for microbe detecting elements arranged behind the measuring surfaces to be removed under sterile conditions and proliferating conditions for the microbes collected by the microbe collecting elements to be subsequently produced. For a sterile removal of the microbe detecting elements from the test chamber, it may be expedient if the microbe detecting elements can be closed with a cover, in particular can be closed in a germ-proof manner.

If a test specimen with vessels as microbe collecting elements is used, after a testing operation the microbes collected in the vessels are preferably cultivated on a solid or liquid nutrient medium, in particular on an agar-containing nutrient medium. As a result, the number of microbes collected in the respective vessels during the testing operation can be determined in an advantageous way, which provides information on a spatial microbe distribution. In this case, it may also be preferred that, after the microbial barrier testing, the microbes collected in the vessels are first diluted with a diluting liquid, such as for example a sodium chloride-peptone solution (maximum recovery diluent), and the cultivation is subsequently carried out with the diluted microbes.

In particular, different pressures or else different temperatures may be set in the test chamber, so that the products can be tested for microbial barrier properties. This may be referred to for example as the testing cycle for the products.

In particular, means for on-line microbe monitoring may also be present in the test chamber. As a result, microbe contamination can be monitored in real time.

Air moving means, in particular blowers or fans, in particular rotorless fans, may be arranged in the test chamber. As a result, a more uniform distribution of the microbes or else a specific non-uniform distribution of the microbes may be produced. Rotorless fans have in particular the advantage that they prevent the microbes from being damaged by rotating rotor blades. In order to produce a uniform distribution of the microbes in the test chamber, the air moving means may be arranged in particular at different locations in the test chamber.

Figure 1:
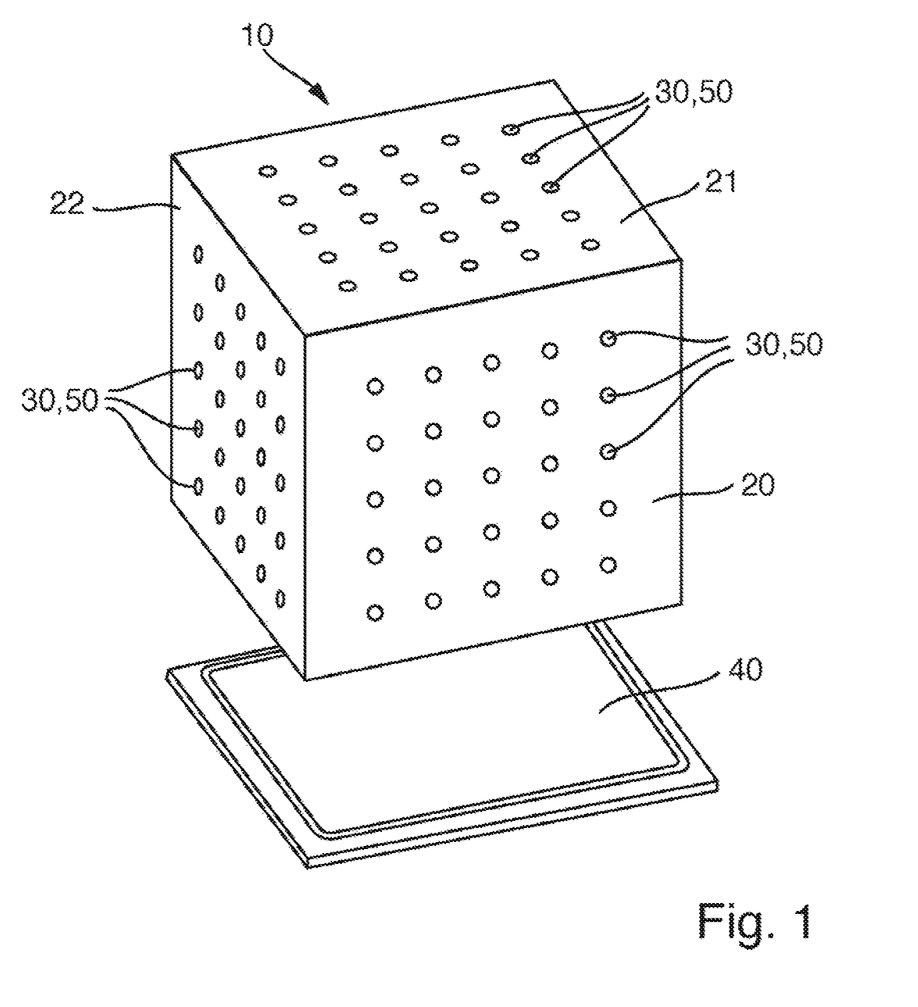
FIG. 1 shows a test specimen according to a first exemplary embodiment.

A person skilled in the art will take further features and advantages from the exemplary embodiments described below with reference to the accompanying figures. In the drawings:

FIG. 1 shows a test specimen 10 according to a first exemplary embodiment of the invention. It is in this case shown in a not completely assembled state.

The test specimen 10 has in the present case a cuboidal form, in particular the form of a cube. In this case, five sides of the cuboid, in particular cube, are used as measuring surfaces, whereas one side of the cuboid, in particular cube, represents a bottom face 40.

In FIG. 1, the measuring surfaces 20, 21, 22 can be seen, while the other surfaces of the cuboid, in particular cube, cannot be seen in FIG. 1 because of the way in which it is represented. They are however formed correspondingly.

On each of the measuring surfaces 20, 21, 22 there are a plurality of microbe collecting elements 30. At each microbe collecting element 30, it is intended that microbes, such as for example bacteria, are collected, and in particular later detected.

For this purpose, in the configuration shown the microbe collecting elements 30 are formed as through-holes 50. To put it another way, the through-holes 50 are formed in the respective measuring surfaces 20, 21, 22, so that at these locations microbes can penetrate in a defined manner through the respective measuring surface 20, 21, 22.

Figure 2:
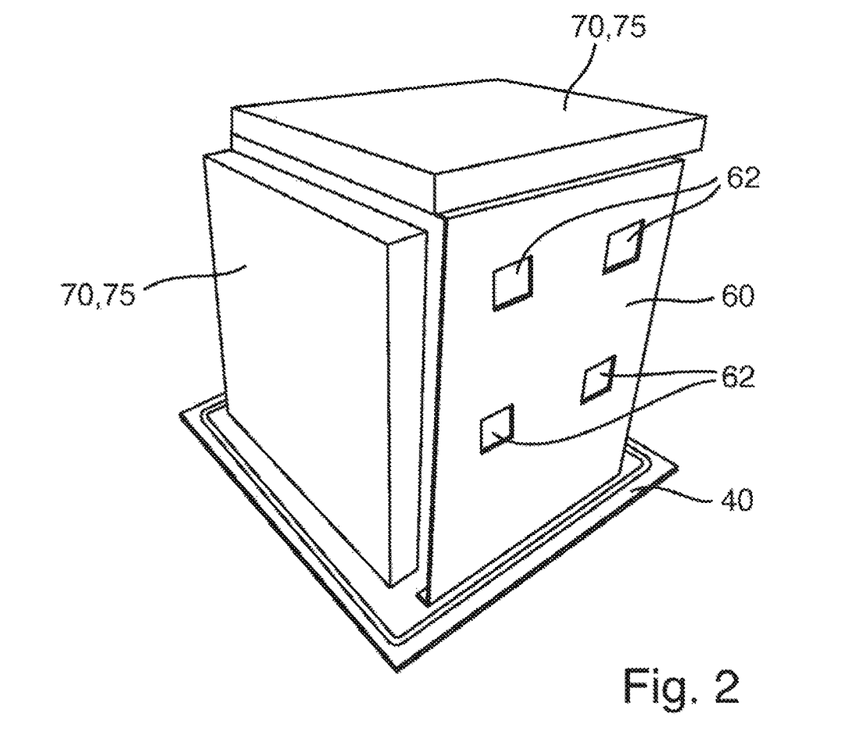
FIG. 2 shows inner components of the test specimen.

FIG. 2 shows components inside the test specimen 10. They are arranged underneath the measuring surfaces 20, 21, 22 represented in FIG. 1.

Holding devices 60, which in the present case are configured with a two-dimensional extent, are arranged on the bottom face 40. Only one of the holding devices 60 can be seen in FIG. 2. Provided in each holding device 60 are a number of clearances 62, which serve for suspending microbe detecting elements in the form of dishes 70. The dishes 70 are in the present case closed with covers 75.

Figure 3:
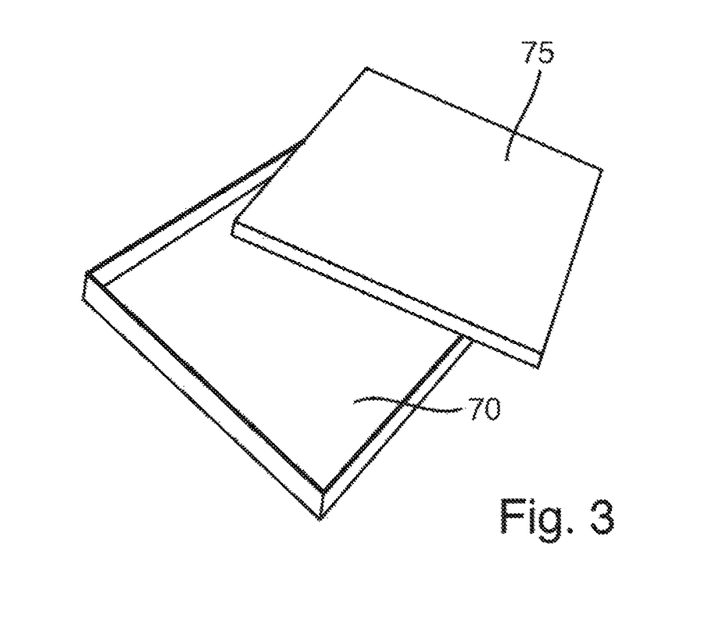
FIG. 3 shows a dish used as a microbe detecting element.

The dishes 70 are formed in the way in which they are separately represented in FIG. 3. It can be seen here that a respective dish 70 can be closed by means of a matching cover 75. Such a state is represented in the case of the dishes 70 in FIG. 2.

Figure 4:
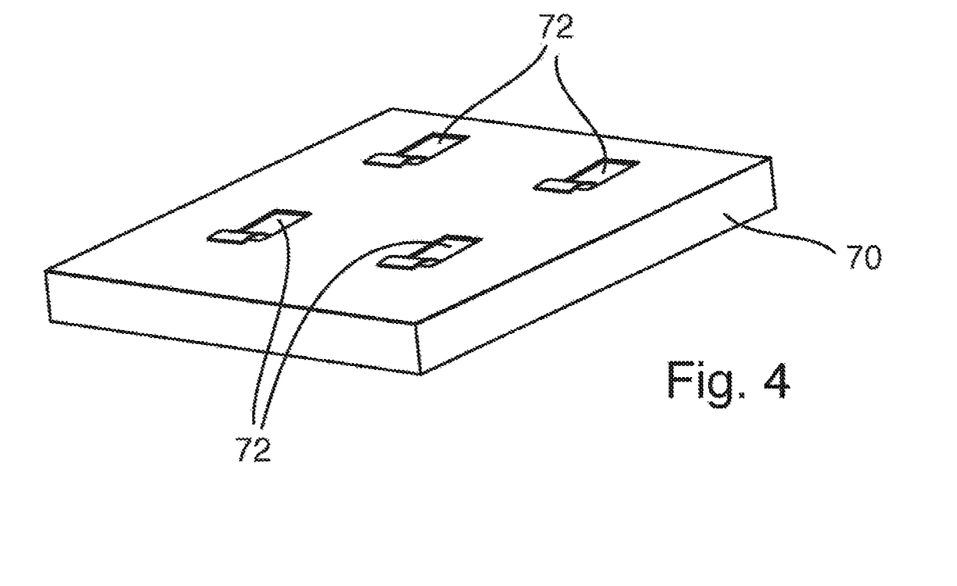
FIG. 4 shows the dish from a rear side.

FIG. 4 shows a dish 70 from a rear side. It can be seen here that the respective dish 70 has on the rear side a number of suspending elements 72, which can be suspended in the clearances 62 of the holding device 60. This allows easy and releasable securement of the dishes 70 on the holding device 60.

Figure 5:
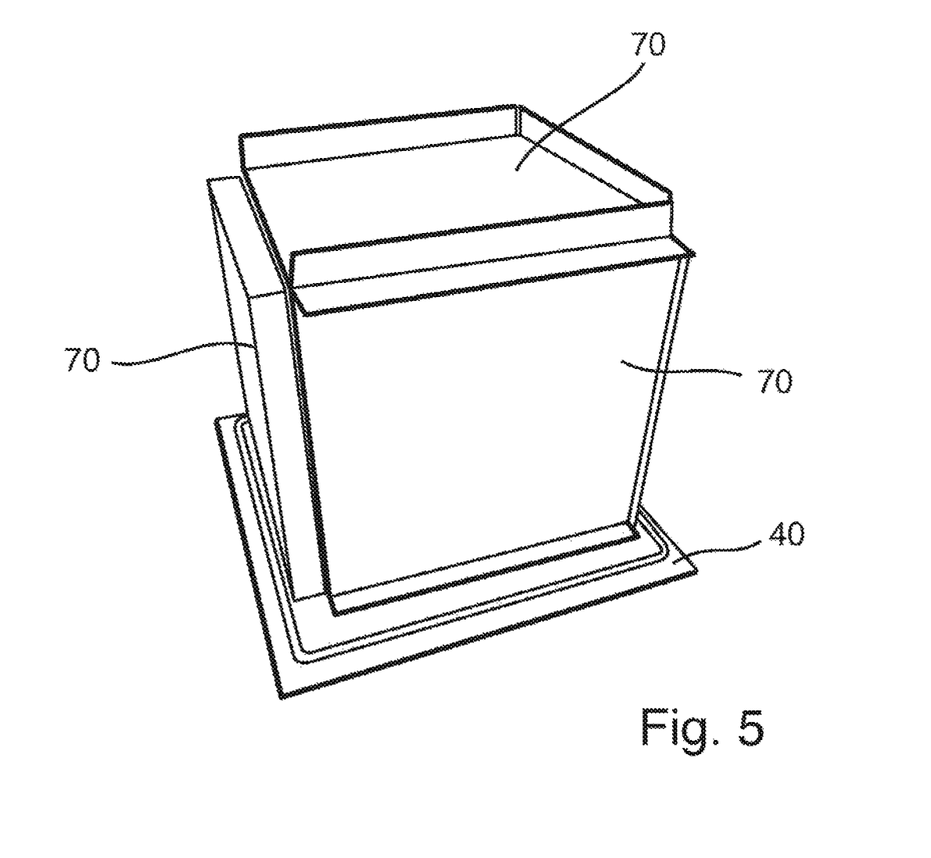
FIG. 5 shows a further view of inner components of the test specimen.

FIG. 5 shows the interior of the test specimen 10, with three dishes 70 that can be seen, without a respective cover. This is a state in which the measuring surfaces 20, 21, 22 can be placed on, so that the cuboid, in particular cube, is closed. Subsequently, microbes can pass through the through-holes 50 and settle on the dishes 70.

The dishes 70 are coated with a nutrient medium, so that a cultivation of the microbes is possible directly on the dishes 70. In this case, the dish 70 that is arranged at the top, i.e. horizontally, is coated with a solid or liquid nutrient medium, while the dishes 70 arranged at the sides, i.e. vertically, are expediently coated with a solid nutrient medium.

Figure 6:
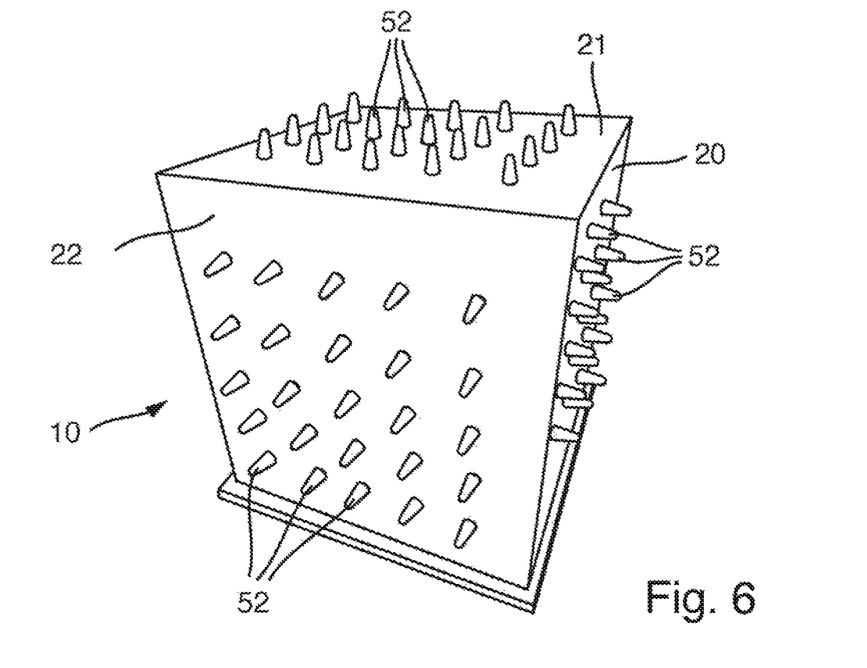
FIG. 6 shows the test specimen in an outer view with closed through-holes.

FIG. 6 shows the test specimen 10 in a state in which it is completely assembled, and in which the through-holes 50 are closed with respective silicone plugs 52. This achieves the effect that a penetration of microbes or other substances through the through-holes 50 is prevented. In such a state, the test specimen 10 can for example be transported in a normal atmosphere, without there being any distortion of a measurement to be carried out afterwards. For example, the test specimen 10 can in this state be introduced into a test chamber, the plugs 52 being removed after the introduction into the test chamber and a possible start of a test.

Figure 7:
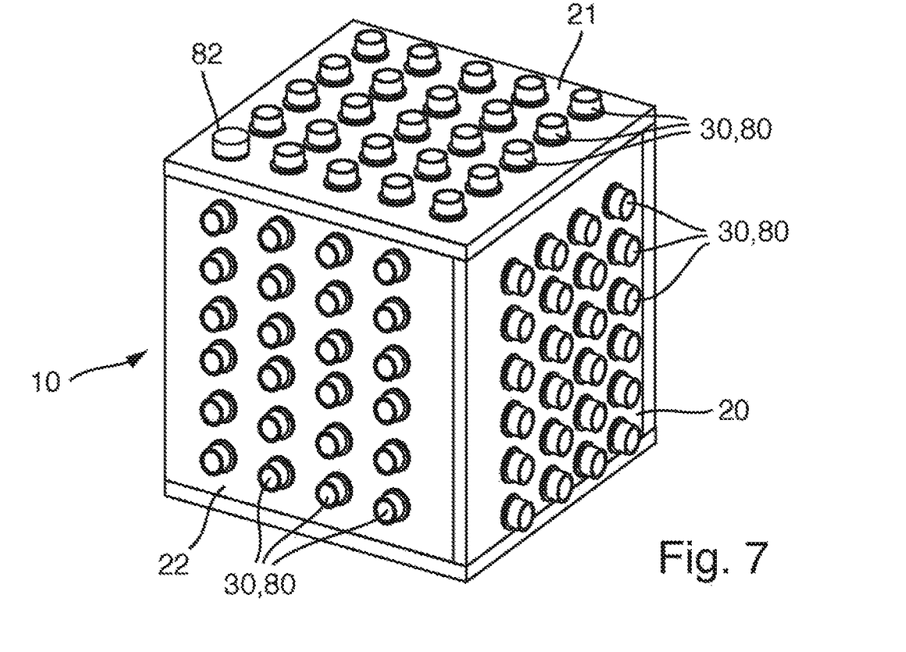
FIG. 7 shows a test specimen according to a second exemplary embodiment.

FIG. 7 shows a test specimen 10 according to a second exemplary embodiment. By contrast with the first exemplary embodiment, in this case the microbe collecting elements 30 are formed as a respective vessel 80, which is secured on the measuring surface 20, 21, 22. The vessels 80 can be covered or can be closed by way of a respective cover 82, which is represented illustratively at one location.

After removing the covers 82, for example after transport and introduction into a test chamber, microbes can enter the vessels 80 and settle there. This allows the microbes to be detected afterwards.

According to the first and second exemplary embodiments, the test specimens 10 have, as shown, in each case multiple measuring surfaces 20, 21, 22, a plurality of microbe collecting elements 30 according to the respective configuration being provided on each measuring surface 20, 21, 22. This allows a three-dimensional microbe distribution to be determined, it being possible for a homogeneity of the microbe distribution in all spatial directions to be tested. It can consequently also be detected whether a product tested in parallel with the test specimen, such as in particular a sterile product packaging, is exposed to microbes from all sides uniformly or in a defined way.

Figure 8:
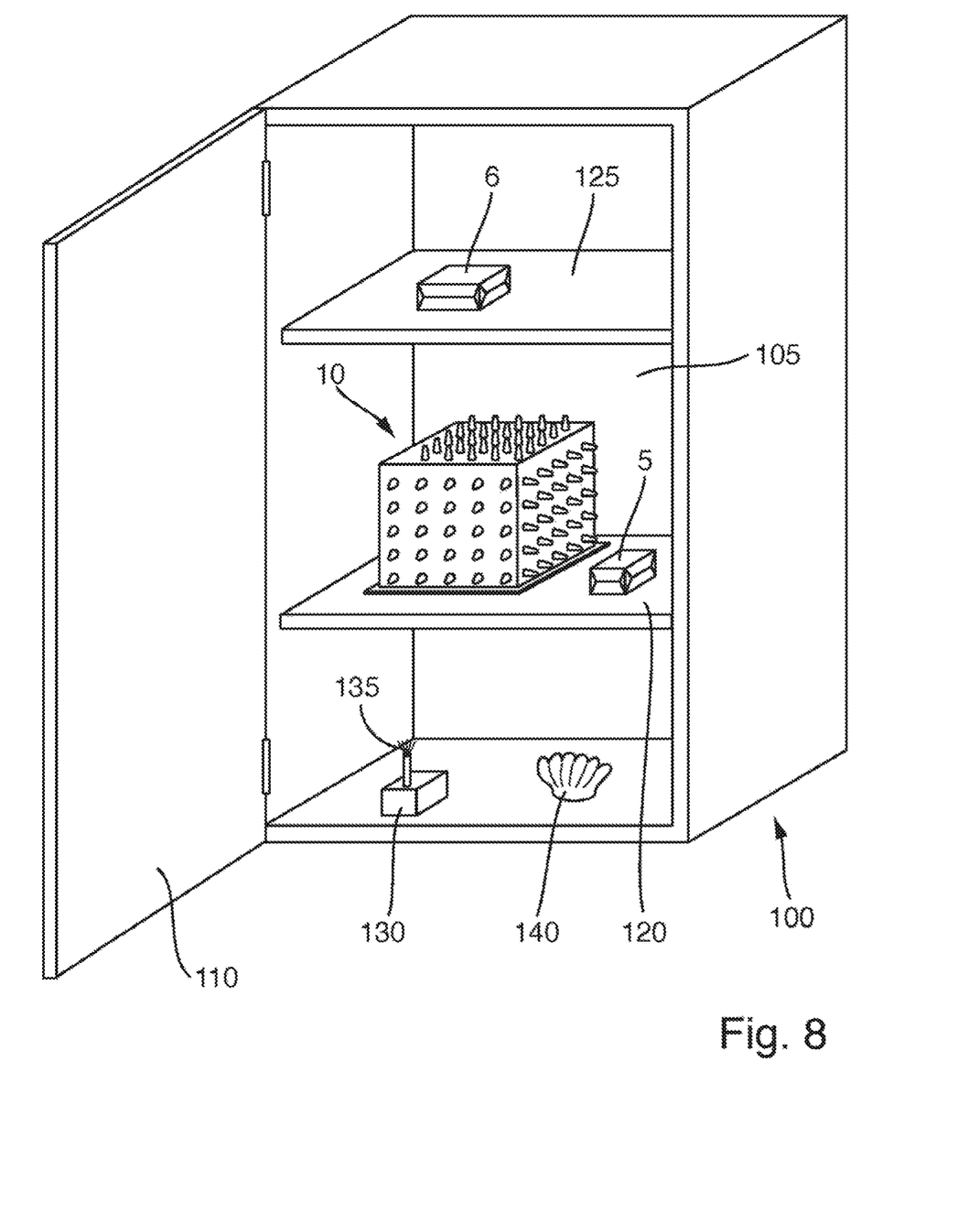
FIG. 8 shows a test chamber.

FIG. 8 shows a test chamber 100 according to an exemplary embodiment of the invention. The test chamber 100 has a test space 105, which can be closed by means of a closing element in the form of a door 110. The test chamber 100 has in the present case two inserted shelves 120, 125, a respective product 5, 6, which is to be tested for microbial barrier properties, being arranged on each inserted shelf 120, 125.

Arranged in the test space 105 is an aerosol generator 130, which is designed to spray an aerosol 135. This aerosol 135 contains microbes, which distribute themselves in the test space 105 and attach themselves inter alia to the products 5, 6. As a result, it can be checked after carrying out a corresponding test whether the microbes can penetrate into the products 5, 6 or through a corresponding sealing of the products.

Also arranged in the test space 105 is a schematic represented bellows 140, which can be externally inflated and reduced in size again. As a result, a pressure inside the test space 105 can be changed. When the test space 105 is closed by means of the door 110, a corresponding pressure tightness is ensured. This allows different pressures to be set in the test space 105, in particular a pressure increase to be performed, and as a result a typical transporting operation with a product 5, 6 to be simulated.

In the test space 105 there is also a test specimen 10 according to the configuration previously described as the first exemplary embodiment. With respect to the exact design of the test specimen 10, reference should be made to the previous statements. The silicone plugs 52 represented in FIG. 6 are still in place in the test specimen 10, so that no microbes can penetrate. If the silicone plugs 52 are removed, microbes can penetrate through the through-holes 50 in the measuring surfaces 20, 21, 22, and accordingly be detected as described further above. This allows a spatial microbe distribution within the test space 105 to be established, and consequently it to be detected during an operation of testing the products 5, 6 whether the microbe contamination for the products 5, 6 was as it should be. This allows much more reliable testing of the products 5, 6 in comparison with for example an earlier practice of carrying out microbe monitoring by means of open petri dishes.

To detect the penetrated microbes, the dishes 70 (or in the case of the second exemplary embodiment the vessels 80) may in particular be exposed after testing has been carried out to proliferating conditions for microbes, so that microbes are cultivated. Each microbe then forms a cell colony, which after some period of time can be optically detected. Alternatively, it is also possible to flush out microbes, for example from the vessels 80, and cultivate them separately. In this case, a dilution is also possible if appropriate, so that even in the case of a high microbe concentration detection of individual microbes remains possible.

After a testing operation, the test space 105 may preferably be disinfected, for example by means of liquid disinfectant, and is thereby prepared for a new use.

The invention claimed is:

1. A method for determining a spatial microbe distribution in a test chamber, the method comprising the following steps:
    (a) introducing a test specimen into the test chamber, wherein the test specimen has a number of measuring surfaces, and a plurality of microbe collecting elements comprising a nutrient medium which are arranged on each of the measuring surfaces;
    (b) introducing a number of products into the test chamber;
    (c) introducing microbes into the test chamber, wherein the plurality of microbe collecting elements comprising the nutrient medium are exposed to the microbes;
    (d) producing outside the test chamber proliferating conditions for microbes collected by the plurality of microbe collecting elements and cultivating the microbes collected by each of the microbe collecting elements the nutrient medium;
    (e) counting cell colonies that have grown on the nutrient medium, thereby determining the number of microbes collected by the plurality of microbe collecting elements; and
    (f) determining the spatial microbe distribution on the basis of the determined number of microbes collected by the plurality of microbe collecting elements, wherein the microbes are bacteria and/or fungi.

2. The method of claim 1, wherein the test specimen has a form of a cuboid, one side of the cuboid forming a bottom face of the test specimen and five sides of the cuboid forming the number of measuring surfaces.

3. The method of claim 2, wherein the cuboid is a cube.

4. The method of claim 1, wherein the test specimen has a bottom face on which the number of measuring surfaces are arranged and wherein said number of measuring surfaces are sloping in relation to the bottom face.

5. The method of claim 1, wherein each of the plurality of microbe collecting elements is formed as a vessel that is secured on each of the number of the measuring surfaces.

6. The method of claim 5, wherein each vessel is assigned a cover, by means of which the vessel can be closed.

7. The method of claim 6, wherein each vessel is closed before the introduction of the test specimen into the test chamber, wherein each vessel is opened after said introduction, and wherein microbes collected by the vessels are cultivated on the nutrient medium, wherein the nutrient medium is a solid or liquid nutrient medium.

8. A method for determining a spatial microbe distribution in a test chamber, the method comprising the following steps:
    (a) introducing a test specimen into the test chamber, wherein the test specimen has a number of measuring surfaces, and a plurality of microbe collecting elements comprising a nutrient medium which are arranged on each of the measuring surfaces;
    (b) introducing a number of products into the test chamber;
    (c) introducing microbes into the test chamber, wherein the plurality of microbe collecting elements comprising the nutrient medium are exposed to the microbes;
    (d) producing outside the test chamber proliferating conditions for microbes collected by the plurality of microbe collecting elements and cultivating the microbes collected by each of the microbe collecting elements on the nutrient medium;

(e) counting cell colonies that have grown on the nutrient medium, thereby determining the number of microbes collected by the plurality of microbe collecting elements and (f) determining the spatial microbe distribution on the basis of the determined number of microbes collected by the plurality of microbe collecting elements, wherein the test specimen has a form of a cuboid, one side of the cuboid forming a bottom face of the test specimen and five sides of the cuboid forming the number of measuring surfaces, and wherein the microbes are bacteria and/or fungi.

* * * * *